United States Patent
Dronzek

(10) Patent No.: US 11,837,342 B2
(45) Date of Patent: Dec. 5, 2023

(54) METHOD AND SYSTEM FOR BACKING UP AND MAINTAINING ELECTRONIC MEDICAL RECORDS FOR PERIODS OF TEMPORARY LOSS OF CONNECTIVITY TO AN ELECTRONIC STORAGE FACILITY

(71) Applicant: Joshua J. Dronzek, Greensburg, PA (US)

(72) Inventor: Joshua J. Dronzek, Greensburg, PA (US)

(73) Assignee: Joshua J. Dronzek, Greensburg, PA (US)

( * ) Notice: Subject to any disclaimer, the term of this patent is extended or adjusted under 35 U.S.C. 154(b) by 764 days.

(21) Appl. No.: 15/800,353

(22) Filed: Nov. 1, 2017

(65) Prior Publication Data

US 2018/0211006 A1 Jul. 26, 2018

Related U.S. Application Data

(60) Provisional application No. 62/534,944, filed on Jul. 20, 2017, provisional application No. 62/450,802, filed on Jan. 26, 2017.

(51) Int. Cl.
| | | |
|---|---|---|
| *G16H 10/60* | (2018.01) | |
| *H04L 67/1097* | (2022.01) | |
| *G06F 12/14* | (2006.01) | |
| *H04L 67/1095* | (2022.01) | |
| *H04L 67/12* | (2022.01) | |

(52) U.S. Cl.
CPC ......... *G16H 10/60* (2018.01); *G06F 12/1408* (2013.01); *H04L 67/1095* (2013.01); *H04L 67/1097* (2013.01); *H04L 67/12* (2013.01); *G06F 2212/1052* (2013.01)

(58) Field of Classification Search
None
See application file for complete search history.

(56) References Cited

U.S. PATENT DOCUMENTS

2007/0180302 A1* 8/2007 Allen ............... G06F 11/2097
714/6.3
2007/0271316 A1* 11/2007 Hollebeek ......... G06F 11/1464
(Continued)

FOREIGN PATENT DOCUMENTS

| CA | 2884970 A1 | 3/2014 |
| CA | 2896088 A1 | 6/2017 |

(Continued)

OTHER PUBLICATIONS

Canadian Office Action; Canadian Intellectual Property Office; Canadian Application No. 2,991,722; dated Aug. 14, 2020; 7 pages.
(Continued)

*Primary Examiner* — Gregory Lultschik
*Assistant Examiner* — William G Lultschik
(74) *Attorney, Agent, or Firm* — Taft Stettinius & Hollister LLP

(57) ABSTRACT

A method and system is disclosed for backing up and maintaining electronic medical records for periods of temporary loss of connectivity between a healthcare facility and an eMAR/eTAR provider storing and maintaining medication administration records and treatment administration records for a healthcare facility.

6 Claims, 6 Drawing Sheets

(56) References Cited

U.S. PATENT DOCUMENTS

| | | | | |
|---|---|---|---|---|
| 2008/0010089 A1* | 1/2008 | DiMaggio | ............... | G16H 40/20 |
| | | | | 705/2 |
| 2011/0025007 A1* | 2/2011 | Butler | .................. | A61G 12/001 |
| | | | | 280/47.35 |
| 2013/0297345 A1* | 11/2013 | Curry | ..................... | G16H 10/60 |
| | | | | 705/3 |
| 2014/0379639 A1* | 12/2014 | Gasser | ................ | H04L 67/2842 |
| | | | | 707/610 |
| 2015/0134359 A1* | 5/2015 | Moskal | ............... | G06F 21/6245 |
| | | | | 705/3 |
| 2016/0117472 A1 | 4/2016 | Padmani et al. | | |

FOREIGN PATENT DOCUMENTS

| | | | |
|---|---|---|---|
| WO | 2009006609 A1 | 1/2009 | |
| WO | 2015034761 A1 | 3/2015 | |

OTHER PUBLICATIONS

Canadian Office Action; Canadian Intellectual Property Office; Canadian Application No. 2,991,722; dated Nov. 7, 2019; 6 pages.

* cited by examiner

FIG. 1 BEST AVAILABLE IMAGE

EMAR Backups

| emar_02_MAR_1.pdf | emar_02_TAR_2.pdf | emar_03_MAR_1.pdf |
| emar_03_TAR_2.pdf | emar_04_MAR_1.pdf | emar_04_TAR_2.pdf |
| emar_05_MAR_1.pdf | emar_06_TAR_2.pdf | emar_06_MAR_1.pdf |

FIG.5

METHOD AND SYSTEM FOR BACKING UP AND MAINTAINING ELECTRONIC MEDICAL RECORDS FOR PERIODS OF TEMPORARY LOSS OF CONNECTIVITY TO AN ELECTRONIC STORAGE FACILITY

RELATED PATENT APPLICATIONS

This application claims priority to Provisional Application No. 62/450,802, filed Jan. 26, 2017, and to Provisional Application No. 62/534,944, filed Jul. 20, 2017.

TECHNICAL FIELD

This invention relates generally to electronic medical records, and more particularly electronic medical records that are maintained and stored at an electronically accessible location that is physically remote from a healthcare/treatment facility that is providing health and medical care to a patient. More particularly, the invention relates to a method and system for backing up and maintaining such electronic records during a period of temporary loss of connectivity between the healthcare/treatment facility and the physically remote storage facility.

BACKGROUND OF THE INVENTION

Hospitals, nursing homes, assisted living facilities and other places which provide health and medical care have long maintained medication administration records, sometimes referred to as MARs, and treatment administration records, sometimes referred to as TARs, to ensure and maintain the correct and orderly administration of medication, treatment and clinical documentation for patients. These institutions are increasingly converting their MARs and TARs to electronic formats. The electronic version of a MAR is commonly referred to as an eMAR, and the electronic version of a TAR is commonly referred to as an eTAR. eMARs and eTARS also are commonly known, both jointly and individually, by the nomenclature EHRs or EMRs or eMARs, short for electronic health/medical records. This electronic data serves as a record for drugs or treatments administered to a patient at a facility, or elsewhere, by healthcare professionals.

eMARs and eTARs are often created on web-based software systems and electronically stored on host servers of eMAR/eTAR providers that are physically remote from the patient's treatment/care facility. All of a patient's healthcare providers have shared electronic access to the servers storing their patient's eMARs and eTARs by way of the internet. Though web-based eMAR/eTAR records are stored on a shared host computer maintained by an eMAR/eTAR, provider, problems arise when the treatment/care facilities are disconnected from the host computer, as for example, when internet service is temporarily interrupted. The loss of connectivity with the host computer, of course, does not alleviate the need to treat/medicate patients at the treatment/care facilities during the period when connectivity is lost.

Past attempts to address the potential loss of connectivity with a remote eMAR/eTAR provider have included local backups at the healthcare facilities. These systems commonly require a special program provided by the eMAR/eTAR provider that is installed on a personal computer located at the healthcare facility. Many of these systems require specialized setup knowledge and are required to comply with detailed system requirements set by the eMAR/eTAR provider. Errors in the setup of such programs can cause the backup records to be incomplete or corrupted, and the systems often lack any alerts or other indications to the healthcare facility that the backup might not be usable. Failure of the backups can be caused by a number of reasons, including failed or incomplete downloading, the primary server being down or being serviced during the time period that the locally installed software tries to retrieve the eMARs or eTARs, or corrupted data. Failures also obviously occur when healthcare facility loses it internet connectivity. Operability of these systems also sometimes require opening of insecure firewall ports on computers at the healthcare facility, constant monitoring of the locally installed programs, and specialized setup of the hard drives for which the local backups are stored to ensure compliance with regulations relating to encryption. Past backup systems also often compromise the confidentiality of a patient's personal health information contained in the backup records. The prior art backup systems have store medical information in a non-encrypted format, and have little, if any, safeguards that prevent unauthorized persons from accessing the backup computer, copying, deleting or modifying information in the data, or even temporarily removing the backup computer to a more private location to confidentiality for more extensive copying.

The invention ensures a healthcare facility has access to sufficient patient specific information and documentation for each of its patients in the event the connectivity between the healthcare facility and the host computer of the eMAR/eTAR provider is lost. The invention securely stores and manages updated and verifiably usable backup data in a file structure that accommodates use by a healthcare facility in the event electronic access to the host computer of the eMAR/eTAR provider is lost.

SUMMARY OF THE INVENTION

One aspect of the invention includes a system for backing up an electronic system that stores medication administration records and treatment administration records on a primary server electronically connected to a healthcare facility. The system includes a computer system located at a healthcare facility and a backup server. The backup server has a secure electronic connection to both the primary server for storing electronic medication administration records and treatment administration records and the computer at the healthcare facility. Though the tasking sequence can be altered, the backup server is configured to perform a variety of tasks including requesting and receiving patient specific medication and/or treatment records from the primary server for patients being treated at the healthcare facility over a secure electronic connection. A determination is made as to whether each record received from the primary server for storage on the backup server is acceptable. This determination is made by opening the record and using a computer-implemented process to determine the record's usability. Timestamps reflecting the time the record was last written upon by the primary server are used to determine whether any received record deemed usable is newer than any record for the healthcare facility that has been previously received from the primary server stored on the backup server. An identifier reflecting the identity of the healthcare facility rendering the medication or treatment to the patient identified in the record is created. A hash value is generated for each record by hashing a plurality of values representative of attributes of the created record, and the record is stored under the hashed value on the backup server in a folder associated with a particular healthcare facility. The values hashed can be, but are not necessarily, values representing the timestamp and the file name. The hashed value then is used to retrieve the file. The system transfers the saved records from the backup server to the computer system at the healthcare in response to a signal reflecting a loss of connectivity between the healthcare facility and the primary server.

In another aspect of the invention, the step of backing up the electronic health/medical records on the backup server includes storing the records in an encrypted format.

In another aspect of the invention, backing up the electronic health/medical records includes opening the records and verifying the completeness and usability of the records prior to storing them on the backup server.

In another aspect of the invention, the verification of the completeness and usability of the records prior to storing them on the backup server is performed by a computer-implemented process.

In another aspect of the invention, the computer-implemented process includes confirming the correctness of the encoding on the record.

In another aspect of the invention, the computer-implemented process includes determining whether the record had experienced any unexpected closing.

In another aspect of the invention, a determination is made of the date and time the record had last been written upon.

In another aspect of the invention, the date and time the record had last been written upon is compared to the date and time of any previously saved version of that record.

In another aspect of the invention, the step of backing up electronic health/medical records from the primary storage system to the backup server includes saving the most recently downloaded version of the record on the backup server only if the date/time timestamp is newer than the time stamp of any previously saved version of the record.

In another aspect of the invention, the step of backing up electronic health/medical records from the primary storage system to the backup server includes maintaining the previously saved version of the record on the server and discarding the most recently downloaded version of the record if the previously saved version is newer than the most recently downloaded version.

In another aspect of the invention, the step of backing up electronic health/medical records from the primary storage system to the backup server further includes storing the downloaded records on the backup server under file names that differ from the file names of the primary storage system.

In another aspect of the invention, the step of backing up electronic health/medical records from the primary storage system to the backup server further includes storing the downloaded records on the backup server under a file name that is created by hashing a plurality of values representative of attributes of the saved record.

In another aspect of the invention, one of the representative values that is hashed with the time stamp of the record reflecting the date and time the record was last written upon by the primary storage system.

In another aspect of the invention, the step of backing up electronic health/medical records from the primary storage system to the backup server by downloading copies of the records on the primary storage system to the backup server includes storing the records on the backup server in a file associated with a healthcare facility which administers medications or treatments to patients to which the records pertain.

In another aspect of the invention, the plurality of secure communication pathways between the backup server and computer system at the healthcare facility includes at least one cellular connection and at least on non-cellular connection.

In another aspect of the invention, a mobile computer system is used for receiving backup medication administration records and treatment administration records at a healthcare facility in the event connectivity between the healthcare facility and a primary server storing electronic medication administration records and treatment administration records is interrupted. The system includes a mobile cart and a processor supported by the mobile cart. The processor has multiple secure connections to a backup server having updated encrypted backup copies of medication administration and/or treatment administration records for patients at the healthcare facility. The processor is programmed to receive encrypted medication administration and/or treatment administration records over one of the secure connections in response to a signal generated in response to an interruption in connectivity between the healthcare facility and a records provider. A display, including an input device associated with the processor is provided for enabling a user to input to the processor and display information on the display. A sensor is associated with the processor for detecting whether the processor is connected to an operative power source. A battery is carried by the mobile cart for providing backup power to the processor, which processor is programmed to utilize power from the battery in response to a signal indicating a lack of power being supplied to the processor. A printer is associated with the processor and the battery, and the processor is programmed to decode encrypted medication administration and/or treatment administration records and actuate printing of the decoded medication administration records and/or treatment administration records in response to a signal indicating electrical power to the processor has been interrupted. The processor also is programmed to selectively print only medication administration records and/or treatment administration records for patients associated with the facility, or subpart thereof, with which the mobile cart is associated.

In another aspect of the invention, the multiple secure connections including at least one cellular connection and at least one non-secular connection.

In another aspect of the invention, the non-cellular connection includes an Ethernet connection.

In another aspect of the invention, the records received by the processor over the secure connection are encrypted, and stored on the processor in encrypted format.

In another aspect of the invention, the input device for the processor and display is a computer peripheral.

In another aspect of the invention, an electronic system stores medication administration records and treatment administration records of a primary server electronically connected to a healthcare facility. The system includes a computer system located at a healthcare facility and a backup server. The backup computer server has a secure electronic connection to both the primary server for storing electronic medication administration records and treatment administration records and the computer at the healthcare facility. The backup server is configured to request and receive patient specific medication and/or treatment records from the primary server over a first secure electronic connection for patients being treated at the healthcare facility. A determination is then made as to whether each record received from the primary server is acceptable for storage on the backup server by opening the record and using a computer-implemented process to determine the record's usability. A determination for each record is made by the computer-implemented process as to whether the record is newer than any previously received record received from the primary server for the healthcare facility stored on the backup server. Each record determined to be both usable by the computer-implemented process and newer than any previously stored record for the healthcare facility is saved. An identifier reflecting the identity of the healthcare facility rendering medication or treatment to the patient identified in the record is created and a hash value is created by hashing a plurality of values representative of attributes of the created record. The record is stored on the backup server in a folder associated with a particular healthcare facility under the hashed value. These records are transfer records from the backup server to the computer system at the healthcare in response to a signal reflecting a loss of connectivity between the healthcare facility and the primary server.

In another aspect of the invention, the computer at the healthcare facility is configured to retrieve selective records of the transferred from the backup server by use of the hashed value.

In another aspect of the invention, a method for using and updating medication administration records and treatment administration records at a treatment facility during periods during periods when electronic communication between the treatment facility and a server storing the records has been compromised includes the steps of electronically transferring copies of medication administration records and treatment administration records from a primary server to a backup server; storing the transferred copies on the backup server in an encrypted format; connecting the backup server to a computer system located at a healthcare facility through at least two independent secure connections; determining whenever an electronic communication connection between the primary server and the healthcare facility has been interrupted; transferring copies of the records on the backup computer to the computer at the healthcare facility in response to a determination the electronic communication connection between the primary server and the healthcare facility has been interrupted; and creating electronic copies of the records transferred to the computer at the healthcare facility.

In another aspect of the invention, the method also includes the step of charting patient specific information pertaining to the medication and/or treatment of patients at the healthcare facility on the electronic records created at the healthcare facility.

In a still further aspect of the invention, a machine-readable interface of an API associated with the charted electronic records is configured to interface and interact with a machine-readable interface on an API associated with the remote electronic medication administration system through a digital network. After the communication connection between the treatment facility and the remote electronic medication administration system has been reestablished, the machine-readable interface on the API associated with the charted electronic records is used to update information records on the primary server.

BRIEF DESCRIPTION OF THE DRAWINGS

While the invention concludes with claims which particularly point out and distinctly claim the invention, it is believed the present invention will be better understood from the following description taken in conjunction with the accompanying drawings, in which like reference numbers identify the same elements in which:

FIG. 5 is a representative screen show of a display of configurable file names that could be presented to persons at a healthcare facility.

Reference will now be made in detail to certain exemplary embodiments of the invention, examples of which are illustrated in the accompanying drawings.

DETAILED DESCRIPTION OF THE
PREFERRED EMBODIMENTS OF THE
INVENTION

Figure 1:
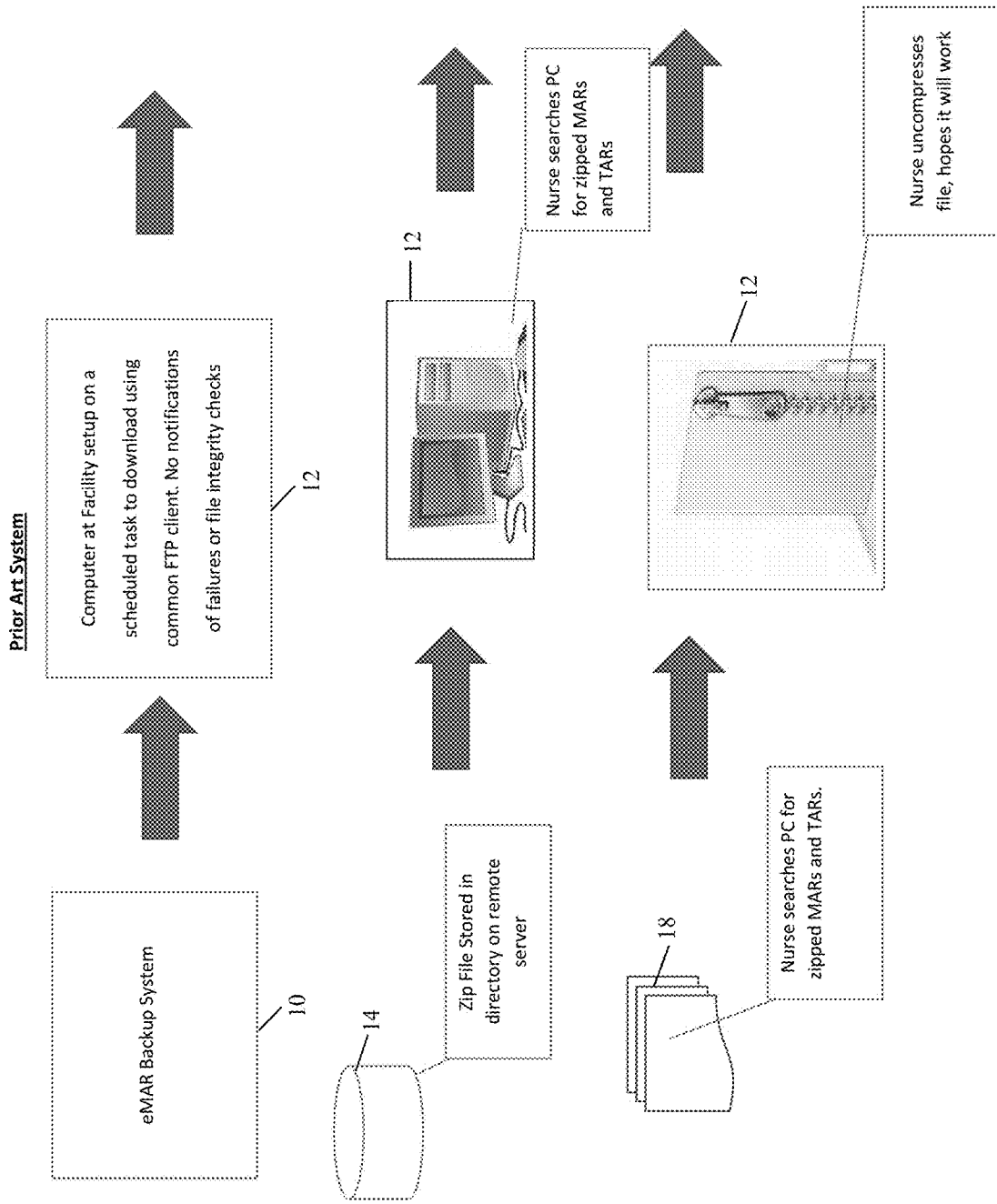
FIG. 1 is schematic depiction showing the operation of a prior art system a healthcare administration record backup system.

Referring now to the drawings, FIG. 1 shows a schematic illustration of a prior art healthcare administration backup system used to backup medication administration records and/or treatment administration records at a healthcare facility for use whenever electronic access to an eMAR/eTAR provider's host computer fails. This backup system, generally designated by the numeral 10 stores backup medication administration records and/or treatment administration records locally on a computer system 12 at a healthcare facility where medication and medical treatments were being provided to patients. These backup records are intended to guide persons administering the medications and performing treatments on the patients in the event the healthcare administration records during periods of time when records maintained on the eMAR/eTAR provider's host computer maintained are inaccessible. A special program, typically provided by the eMAR/eTAR provider, downloads compressed versions of the records to the computer system 12 at the healthcare facility on a scheduled basis. These records were typically transferred over an unsecured FTP connection between the computer system 12 located at the healthcare facility and the eMAR/eTAR's provider's host computer.

As schematically shown in FIG. 1 by numeral 14, the remote host computer of the eMAR/eTAR provider typically stores healthcare administration records in lossless data compression files, such as, but not necessarily, a .ZIP files. The records typically are downloaded from the eMAR/eTAR provider's host computer 14 in this format, and similarly stored on the backup computer 12 at the healthcare facility in the same compressed format.

Due to complexities associated with internet security, the installation of these types of prior art programs at a healthcare facility typically requires considerable computer expertise. In order for the programs to work properly, strict compliance with a long list of system requirements is necessary, and insecure firewall ports of the computer at the healthcare facility sometimes needed to be opened to effectuate communication with the eMAR/eTAR host computer 14. Since the operability of some prior art backup systems was strictly dependent upon proper configuration of the program installed on the computer system 12, incorrect firewall or router settings could cause the downloaded backup records to be incomplete or otherwise prevent the recovery of complete records. Often times, the incompleteness or non-usability of the records is not discovered until it is too late, i.e., until after electronic connectivity between the local computer system 12 and the remote host computer is lost, and the nurse or other medical personal searches and attempts to retrieve the stored file from the local backup computer system 12. More particularly, it is not until the retrieved file is decompressed (as represented by the icon designated by numeral 20) that the record is found to be unusable.

Figure 2:
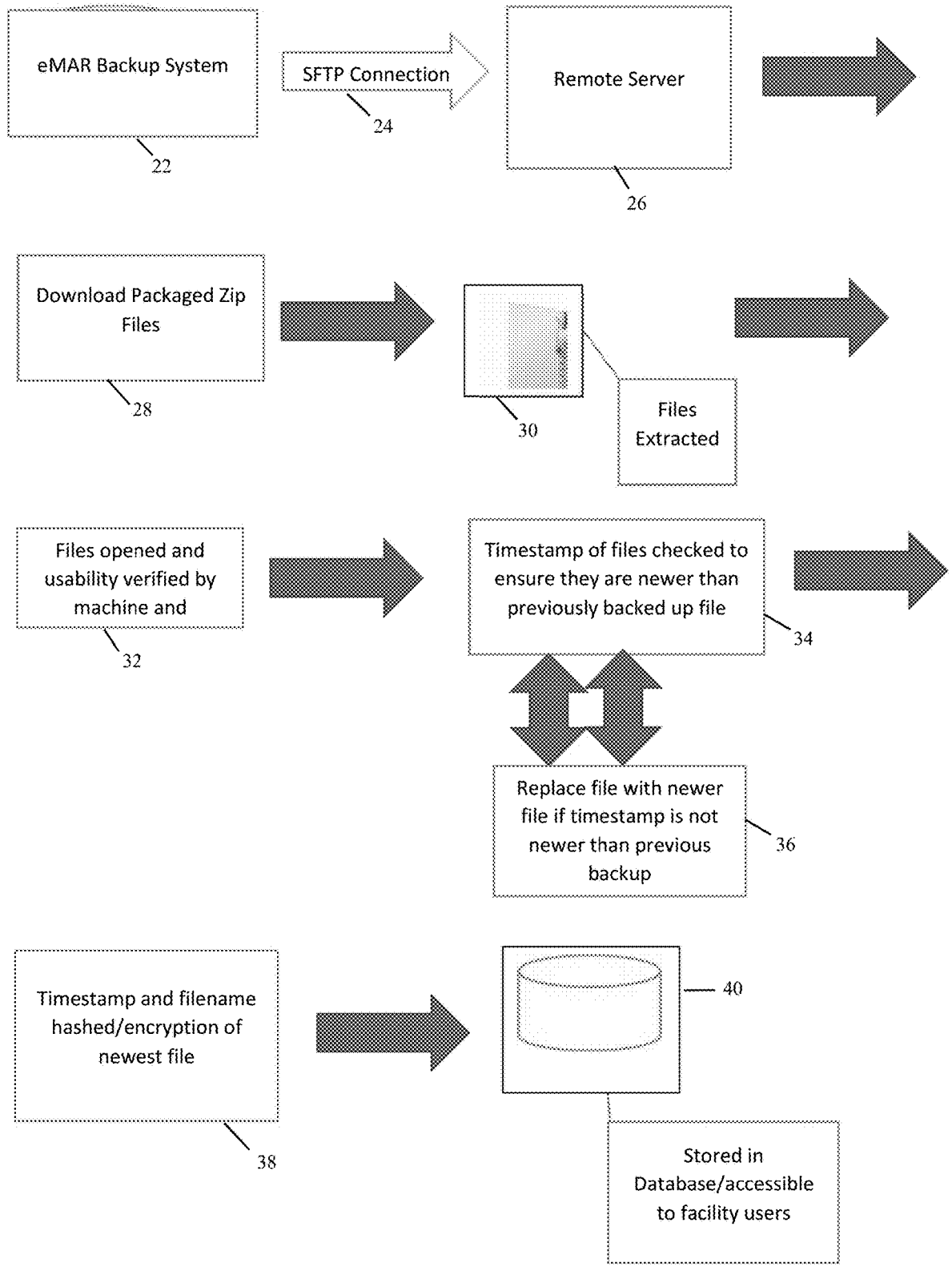
FIG. 2 is schematic depiction showing the operation and functionality of an exemplary backup system arranged in accordance with the principles of the invention.

Turning now to FIG. 2, one form of a healthcare administration records backup system 22 arranged in accordance with the principles of the present invention is schematically depicted. As shown by arrow 24, the backup system 22 of the present invention is connected to a server 26 maintained by an eMAR/eTAR provider over a SFTP connection using Secure Transfer Protocol. Unlike FTP, SFTP (Secure Transfer Protocol) is a packet-based transfer protocol. The files are downloaded from the eMAR/eTAR provider in a compressed format, such as, but not necessarily, a .Zip file, as depicted by numeral 28. Once a compressed file is received by the backup system, however, the files are extracted, as schematically shown with numeral 30, and opened with a computer script, as schematically shown by numeral 32. A script run by backup computer system 22 then verifies the completeness and usability of the opened files through any number of script-initiated computer-implemented integrity testing process. In one preferred form of the invention, the computer-implemented integrity testing process includes inspecting and confirming the encoding of the record, and determining if the file had experienced unexpected closure. Such computer-implemented processes are known to those skilled in the art.

If a file passes these computer-implemented integrity testing processes, it is determined to be complete and usable. For each file received from the eMAR/eTAR provider's host computer by the backup system 22 that is determined to be complete and usable, a time stamp on the file reflecting the date and time on which the file had last been written upon by the eMAR/eTAR provider is read. The backup computer system 22 then compares the timestamp for the most recently received record against any version of the same file previously saved by the computer system 22. As depicted by the blocks 34, 36, if the timestamp reflecting the time the file had last been written upon by the eMAR/eTAR provider is newer than the timestamp of the previously saved version, the newly downloaded version of the file is saved on the computer system 22 over the previously save version of the file. If, on the other hand, the timestamp reflecting the time the file had last been written upon by the eMAR/eTAR provider is older than the time stamp reflecting the time the previously saved version of the file was received by computer system 22, indicating a lack of activity in the time period since the previous version had been saved, the previously saved file is maintained on the computer 22, and the more recently downloaded version disregarded.

When files are saved on the computer system 22, they once again saved as compressed files, such as zip files. They are, however, saved with a different file structure than that used by the host computer of the eMAR/eTAR provider. Specifically, the saved files are compressed (preferably zipped) and stored in folders which correspond to a specific healthcare facility (or a portion thereof) under identifying file names that are secure and which correlate with a specific healthcare facility (or portion thereof).

The identifying file name used to store and retrieve the saved records is created by a hashing algorithm which hashes a plurality of values representative of attributes of the created record. Two attributes that are hashed in one of the preferred embodiments are the timestamp and file name, as depicted by block 38. The encrypted file is then stored in a healthcare administration record emergency backup database 40 accessible to healthcare facility users. The hash value is then used to retrieve the file from the database 40. In this way, the file is fully encrypted whenever it is saved on the backup system 22.

Though the media storing the database 40 can reside at the healthcare facility, it is not necessary for the storage media to be physically at that location. It is often more efficient to store backup files remotely, and to store backup files for multiple facilities at a common location and on a common backup server. When this is done, however, it is imperative to provide multiple independent secure connections between the healthcare facility and the backup server where the database 40 is stored to ensure the healthcare has access to the backup records whenever connectivity between the healthcare facility and the host server of the eMAR/eTAR provider is lost. Locating the database 40 at a remote location also provides the backup data to be located at a physically secure facility, and assists in maintaining the confidentiality of patient health information and compliance with healthcare information confidentiality requirements. Additionally, the use of the present invention has audit trail capability, and can track any person who sees, opens or modifies data in the program.

Figure 3:
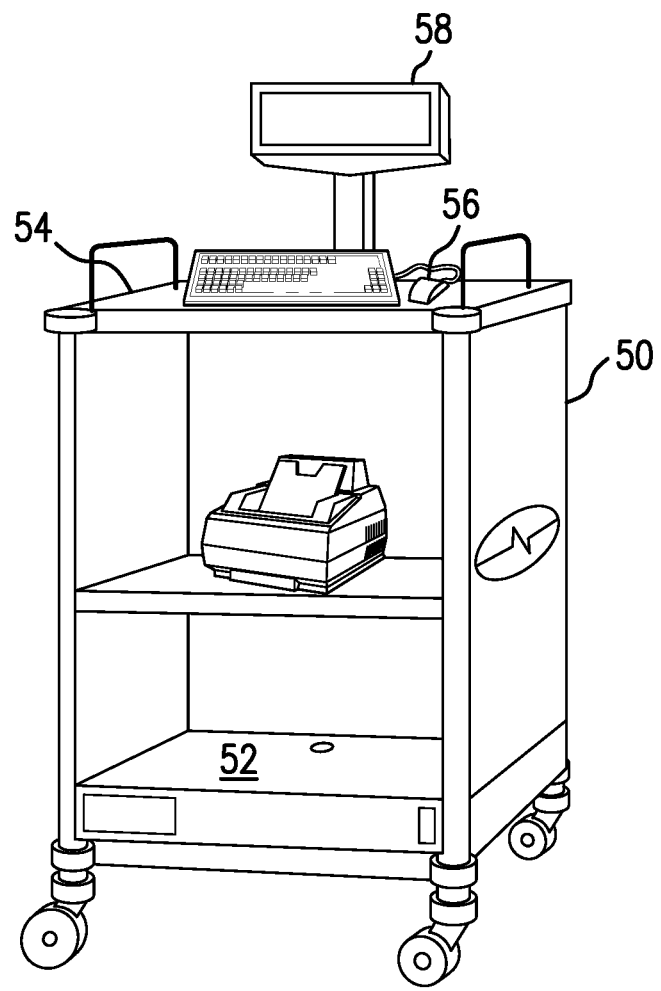
FIG. 3 is a schematic representation of a mobile cart that can be located at a healthcare facility and used to interface with an emergency backup system in the event connectivity between the healthcare facility and a host computer of an eMAR/eTAR provider is lost.

FIG. 3 shows an emergency management device 50, specifically illustrated as a mobile cart 50, employing one aspect of the invention. The cart 50, which preferably is located at a healthcare facility which administers and/or treats patients, has at a processor 52 with multiple inputs devices, such as a keyboard 54 and a mouse 56. A display 58 associated with the processor 52, keyboard 54 and mouse 56 is provided. A printer 58 also is optionally carried by the mobile cart 50. As those skilled in the art will readily appreciate, other types of inputs to the processor 52, such as a touch display, can be used in lieu of the described configuration.

Figure 4:
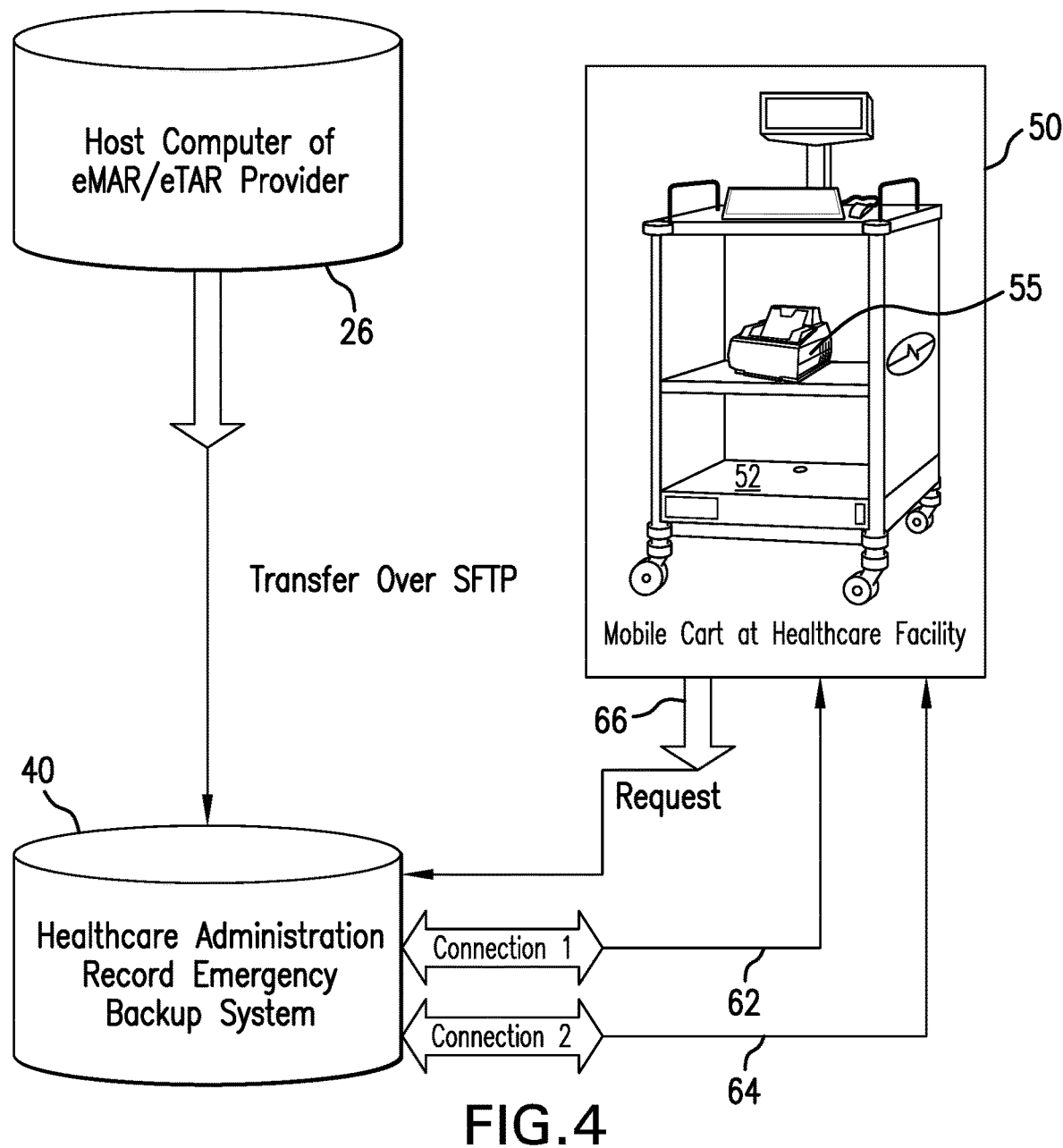
FIG. 4 is a schematic representation showing the relationship between a mobile cart located at a healthcare facility, a host computer of an eMAR/eTAR provider, and an administration record backup system.

As depicted in FIG. 4, the processor 52 is connected to the remotely healthcare administration emergency backup server 40 by a plurality of secure connections, represented by arrows 62 and 64. The secure connections 62 and 64 are independent of each other so that a failure of one of the connections does not impair the connectivity of the other(s). These independent connections may include, for example, a first non-cellular connection, such as a wired ethernet or wireless connection 62 and a second connection 64 over a dedicated secure cellular network. Downloads from the database 40 to the processor 52 can be initiated either a pull method, in response to a request (as represented by arrow 66) from processor 52, or by a push method in which the computer system associated with the healthcare administration emergency backup service pushes backup files to computer 52 whenever there is a failure of the connection between the healthcare facility and the eMAR/eTAR provider. The computer system carried by the mobile cart 50 is separate from and independent of the primary system at the healthcare facility used to communicate with the eMAR/eTAR provider when there is connectability between the healthcare facility and the eMAR/eTAR provider.

In the event the healthcare facility is unable to connect with the remote host computer 26 of the eMAR/eTAR provider (see FIGS. 2 and 4), due for example to an internet outage at the healthcare facility, the healthcare facility utilizes the emergency backup system 40 to obtain medication and treatment information necessary to maintain care and treatment of its patients during the outage. Rather than communicating with the host computer 26 of the eMAR/eTAR provider, the emergency management device 50 electronically communicates with the healthcare administration emergency system 40. As one of many options to simply communicate the initiation of communication between the healthcare administration emergency system 40 and the emergency management device 50, a dedicated specialized operating system can be installed on the processor 52 so that communications with the healthcare administration emergency system 40 is initiated in response to turning on the power switch of the processor 52. Alternatively, a person at the healthcare facility can hit an emergency mode button on the processor to initiate transfer of information between the healthcare administration emergency system 40 and the emergency management device 50. In any event, downloading of relevant eMARs and eTARs associated with the healthcare facility to the processor 52 from the backup server 40 is initiated in response to a loss of connection between the healthcare facility and the host server 26 of the eMAR/eTAR provider. As noted above, the emergency backup system 50 stores compressed eMARs and eTARs associated with a specific facility in a folder which corresponds to that facility. Even if the eMAR/eTAR provider loses all connectivity (including communications to the emergency management backup system 50), the emergency management backup system 50 will still have a local copy of the patient records and send notifications to the facility that a backup has failed.

As shown in FIG. 5, the files downloaded to the processor 52 have configurable names, so that a nurse or other person at the healthcare facility assign file names to allow nurses logging into their system to easily identify their wing or unit. Renaming the file names can be achieved by clicking on an menu associated with each file.

The emergency management backup system 50 also can be configured to automatically print each of the eMARs and eTARs downloaded into processor 52. The printing could occur at the printer 55 carried by the cart 50, or at any other secure location of the healthcare facility's choosing.

Figure 6:
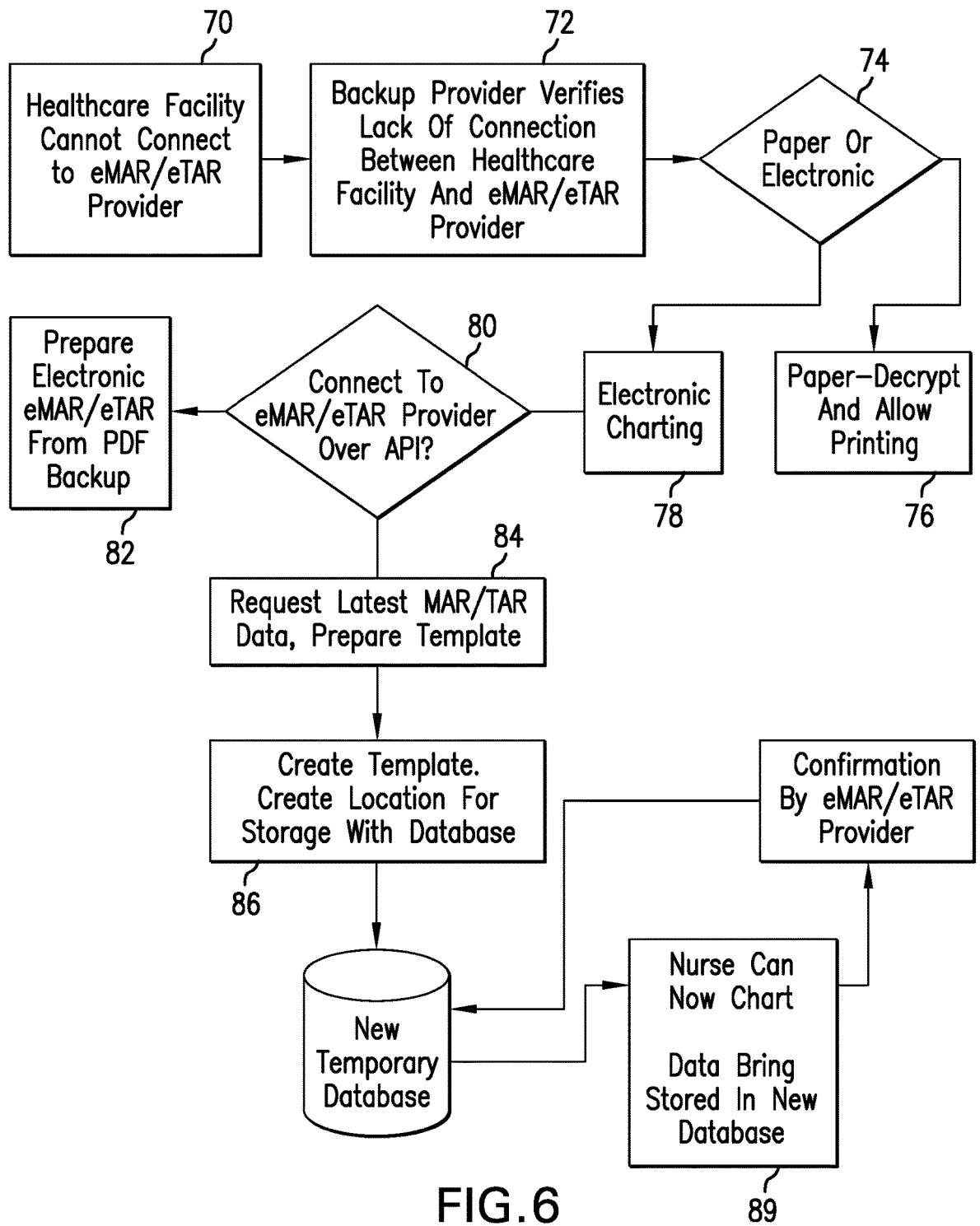
FIG. 6 is a flowchart showing various temporary charting options available to personnel at healthcare facilities for patients at the healthcare facility.

It there is loss of connectivity to the host computer of the eMAR/eTAR computer over an extended time, it might be desirable to continue to electronically chart, or document, any medications or treatments provided by the healthcare facility during the period backup records are being used. This electronic charting can occur in at least two ways, as schematically shown in FIG. 6. In if the healthcare facility cannot connect to the eMAR/eTAR provider, as represented by block 70, the healthcare administration emergency backup server 40 verifies the lack of connectivity, as represented by block 72. Depending upon the option selected by the healthcare facility, as schematically shown by decision block 74, the backup eTARs and eTARs can be retrieved, decompressed and printed for use in a paper format, as shown by block 76. Alternatively, the healthcare facility can elect to use electronic charting, as represented by block 78. When this option is selected, the downloaded files, typically in pdf format, are used to generate an electronic copy. This electronic copy is then charted during the duration of the loss of connectivity to the eMAR/eTAR provider's host computer.

Once connectivity is once again established, it is necessary to communicate the information charted on the backup file to the eMAR/eTAR provider. This can be achieved in a number of ways, as represented by decision block 80. For example, one option, is to prepare an electronic eMAR/eTAR that can be printed off to be uploaded to the eMAR/eTAR provider's host computer once connectivity with that host computer is re-established, and the primary eMAR/eTAR system becomes operational. This option is depicted in the box 82.

Another option is to provide an application program interface ("API") that allows communication between the healthcare administration emergency system 40 and the eMAR/eTAR host computer. The connection can be either one-way or bidirectional, so that either the eMAR/eTAR provider or healthcare facility can initiate the communication. With an API, the processor 52 on cart 50 takes the latest MAR/TAR data from the healthcare administration record emergency backup system 40, and creates a template (as depicted in block 84), which is populated with the eMAR/eTAR data from the backup file with the latest date. As shown in block 86, a database storage location is then created for a temporary database 88. As schematically represented by block 90, nurses can then use the mobile cart 50 to enter new medication/treatment data into the temporary database 88. Once re-establishment of the connectivity between the healthcare facility and the host computer 26 of the eMAR/eTAR provider is confirmed by the emergency backup system 40, the updated data is put in a format compatable with the host computer 26, and submitted to the eMAR/eTAR provider. Those skill in the art will undoubtedly appreciate that, though the communication between the eMAR/eTAR provider and healthcare facility is specifically disclosed in connection with a computer system mounted on a mobile cart, this aspect of the invention is not in any way limited to a mobile cart embodiment, and is applicable to any type of computer system at the healthcare facility in communication with the emergency healthcare system 50.

The foregoing description of the preferred embodiments of the present invention have been presented for purposes of illustration and description. It is not intended to be exhaustive or to limit the invention to the precise form disclosed. Obvious modifications or variations are possible in light of the above teachings. For example, the sequencing of the activities can vary from that described in the described embodiments, and except when specifically noted or necessarily implied, nothing in the specification or claims is intended to be restricted to any particular sequence of activities. As a further example, the invention was described with the use of a mobile cart at the healthcare facility. Those skilled in the art will readily appreciate that the invention is not limited to the use of a mobile cart. It will be further appreciated that the disclosed invention includes a number of different aspects, which can be employed separately or together. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breath to which they are fairly, legally and equitably entitled. The drawings and preferred embodiments do not and are not intended to limit the ordinary meaning of the claims in their fair and broad interpretation in any way.

What is claimed is:

1. A method for using and updating medication patient health information records at a healthcare facility during periods when electronic communication between the treatment facility and a primary eMAR/eTAR system storing the medication patient health information records has been compromised, comprising:

electronically transferring patient health information data associated with the medication patient health information records from the primary eMAR/eTAR system associated with the healthcare facility to a healthcare administration emergency backup server;

storing the transferred patient health information data on the healthcare emergency backup server to prevent unauthorized access to the patient information data;

initiating communications between the healthcare administration emergency management backup server and the emergency management device when a user at the healthcare facility activates an emergency mode button positioned on the emergency management device to initiate the transfer of information between the healthcare administration emergency backup server and the emergency management device;

connecting the healthcare administration emergency backup server to an emergency management device located at the healthcare facility through at least two independent secure connections, wherein a first independent secure connection is a cellular connection and a second independent secure connection is a non-cellular connection;

determining when an electronic communication connection between the primary eMAR/eTAR system and the healthcare facility has been interrupted;

initiating communications between the emergency management device and the healthcare administration emergency backup server and downloading patient health information data from the healthcare administration emergency backup server in response to a determination that the electronic communication connection between the primary eMAR/eTAR system and the healthcare facility has been interrupted;

providing an Application Program Interface (API) to enable bidirectional communication between the primary eMAR/eTAR system and the healthcare administration backup server;

providing the patient health information data from the healthcare administration backup server as downloaded from the primary eMAR/eTAR system via the API to the emergency management device;

generating a template that is populated with the patient healthcare information data from a user and is stamped with a date;

automatically printing, at the emergency management device, the patient information health data downloaded from the health care administration emergency backup server, wherein only patient health information data for patients associated with the healthcare facility with which the emergency management device is associated is printed;

creating a database storage location in a temporary database thereby enabling the user to enter subsequent patient health information developed during treatment of a patient by the user into the emergency management device via the temporary database;

electronically charting the patient health information data, by a user inputting subsequent patient health information developed during treatment of a patient by the user into the emergency management device located at the healthcare facility in response to the determination that the electronic communication connection between the primary eMAR/eTAR system and the healthcare facility has been interrupted, wherein the emergency management device stores the patient information data for a plurality of patients of the healthcare facility that are examined by the user when the electronic connection between the primary eMAR/eTAR system and the healthcare facility has been interrupted;

storing on the healthcare administration emergency backup server subsequent patient information data created and stored by the emergency management device located at the healthcare facility as obtained during treatment of the plurality of patients of the healthcare facility by the user that are examined by the user during a period of time when the electronic communication connection between the primary eMAR/eTAR system and the healthcare facility is interrupted, wherein the subsequent patient information data stored by the emergency management device is provided to the healthcare administration emergency backup server via the first independent secure connection and/or the second independent secure connection; and in response to an indication that the electronic communication connection between the healthcare facility and the primary eMAR/eTAR system has been reinstated, transferring from the healthcare administration emergency backup server to the primary eMAR/eTAR system the subsequent patient information data created and stored on the healthcare administration emergency backup server as obtained during treatment of the plurality of patients of the healthcare facility by the user that are examined by the user during the period of time when the electronic communication connection between the primary eMAR/eTAR system and the healthcare facility was interrupted.

2. A method as recited in claim 1 further comprising the step of charting patient specific information pertaining to medication or treatment of patients at the healthcare facility on the electronic records created at the healthcare facility.

3. A method for using and updating medication patient health information records at a healthcare facility during periods when electronic communication between the healthcare facility and a primary eMAR/eTAR system storing the medication patient health information records has been compromised, comprising:

electronically transferring records from the primary eMAR/eTAR system associated with the healthcare facility to a healthcare administration emergency backup server to prevent unauthorized access to the patient health information data when stored on the healthcare administration emergency backup server;

initiating communications between the healthcare administration emergency management backup server and the emergency management device when a user at the healthcare facility activates an emergency mode button positioned on the emergency management device to initiate the transfer of information between the healthcare administration emergency backup server and the emergency management device;

determining when an electronic communication connection between the primary eMAR/eTAR system and the healthcare facility has been interrupted;

initiating communications between an emergency management device and the healthcare administration emergency backup server and downloading patient health information data from the healthcare administration emergency backup server in response to a determination that the electronic communication connection between the primary eMAR/eTAR system and the healthcare facility has been interrupted;

providing an Application Program Interface (API) to enable bidirectional communication between the primary eMAR/eTAR system and the healthcare administration backup server;

providing the patient health information data from the healthcare administration backup server as downloaded from the primary eMAR/eTAR system via the API to the emergency management device;

generating a template that is populated with the patient health information data from a user and is stamped with a date;

automatically printing, at the emergency management device, the patient information health data downloaded from the health care administration emergency backup server, wherein only patient information heath data for patients associated with the healthcare facility with which the emergency management device is associated is printed;

creating a database storage location in a temporary database thereby enabling a user to enter subsequent patient health information data developed during treatment of a patient by the user into the emergency management device via the temporary database;

connecting the healthcare administration emergency backup server to an emergency management device located at the healthcare facility through at least two independent secure connections, wherein a first independent secure connection is a cellular connection and a second independent secure connection is a non-cellular connection;

electronically charting the patient health information data, by the user inputting subsequent patient health information data developed during treatment of the patient by the user into the emergency management device in response to the determination that the electronic communication connection between the primary eMAR/eTAR system and the healthcare facility has been interrupted, wherein the emergency management device stores the patient information data for a plurality of patients of the healthcare facility that are examined by the user when the electronic communication connection between the primary eMAR/eTAR system and the healthcare facility has been interrupted;

storing on the healthcare administration emergency backup server the subsequent patient health information data created and stored by the emergency management device as obtained during treatment of the plurality of patients of the healthcare facility by the user that are examined by the user during a period of time when the electronic communication connection between the primary eMAR/eTAR system and the healthcare facility is interrupted; and in response to an indication that the electronic communication connection between the healthcare facility and the primary eMAR/eTAR system has been reinstated, transferring from the healthcare administration backup server to the primary eMAR/eTAR system the subsequent patient health information data created and stored as obtained during treatment of the plurality of patients of the healthcare facility by the user of the healthcare facility that are examined by the user during the period of time when the electronic communication connection between the primary eMAR/eTAR system and the healthcare facility was interrupted.

4. The method of claim 3, further comprising:
installing an operating system on the emergency management device so that communications between the healthcare administration emergency backup server and the emergency management device are initiated when activating power to the emergency management device.

5. A system for using and updating medication patient health information records at a healthcare facility during periods of when electronic communication between the healthcare facility and a primary eMAR/eTAR system storing the medication patient healthcare information records has been compromised, comprising:

an emergency management device configured to:
download patient health information data in response to a determination that the electronic communication connection between the primary eMAR/eTAR system and the healthcare facility has been interrupted;

receive patient health information data as downloaded from the primary eMAR/eTAR system via an Application Program Interface (API), generate a template that is populated with patient healthcare information data from a user and is stamped with a date, automatically print, at the emergency management device, the patient information health data download from the health care administration emergency backup server, wherein only patient health information data for patients associated with the healthcare facility with which the emergency management device is associated is printed, create a database storage location in a temporary database thereby enabling the user to enter subsequent patent health information data developed during treatment of a patient by the user via the temporary database, and electronically chart the patient health information data, by the user inputting subsequent patient health information data developed during treatment of the patient by the user into the emergency management device in response to the determination that an electronic communication connection between the primary eMAR/eTAR system and the healthcare facility has been interrupted, wherein the emergency management device stores the patient information data for a plurality of patients of the healthcare facility that are examined by the user when the electronic communication between the primary eMAR/eTAR system and the healthcare facility has been interrupted; and a healthcare administration emergency backup server is configured to:
provide the API to enable bidirectional communication between the primary eMAR/eTAR system and healthcare administration emergency backup server, receive transfer records electronically transferred from the primary eMAR/eTAR system associated with the healthcare facility to the healthcare administration emergency backup server to prevent unauthorized access to the patient health information data when stored on the healthcare emergency backup server, initiate communication between the healthcare administration backup server and the emergency management device when a user at the healthcare facility activates an emergency mode button positioned on the emergency management device to initiate the transfer of information between the healthcare administration emergency backup server and the emergency management device;

connect to the emergency management device through two independent secure connections, wherein a first independent secure connection is a cellular connection and a second independent secure connection is a non-cellular connection, provide the patient health information data as downloaded from the primary eMAR/eTAR system via the API to the emergency management device, determine when the electronic communication connection between the primary eMAR/eTAR system and the healthcare facility has been interrupted and provide patient health information data to the emergency management device in response to the determination that the electronic connection between the primary eMAR/eTAR system and the healthcare facility has been interrupted, store the subsequent patient health information data created as provided by the emergency management device as obtained during treatment of the plurality of patients of the healthcare facility by the user that are examined by the user during a period of time when the electronic connection between the primary eMAR/eTAR system and the healthcare facility is interrupted, wherein the subsequent patient information data stored by the emergency management device is provided via the first independent secure connection and/or the second independent secure connection, and in response to an indication that the electronic communication connection between the healthcare facility and the primary eMAR/eTAR system has been reinstated, transfer to the primary eMAR/eTAR system the subsequent patient health information data created and stored as obtained during treatment of the plurality of patients of the healthcare facility by the user that are examined by the user during the period of time when the electronic communication connection between the primary eMAR/eTAR system and the healthcare facility was interrupted.

6. The system of claim 5, wherein the healthcare administration emergency backup server is further configured to initiate communications between the healthcare administration emergency backup server and the emergency management device when power is activated to the emergency management device.

* * * * *